(12) United States Patent
Kehler

(10) Patent No.: US 8,492,394 B2
(45) Date of Patent: Jul. 23, 2013

(54) (3-ARYL-PIPERAZIN-1-YL), (2-ARYL-MORPHOLIN-4-YL) AND (2-ARYL-THIOMORPHOLIN-4-YL) DERIVATIVES OF 6,7-DIALKOXY-QUINAZOLINE, 6,7-DIALKOXYPHTALAZINE AND 6,7-DIALKOXYISOQUINOLINE AS PDE10A ENZYME INHIBITORS

(75) Inventor: Jan Kehler, Lyngby (DK)

(73) Assignee: H. Lundbeck A/S, Valby (DK)

( * ) Notice: Subject to any disclaimer, the term of this patent is extended or adjusted under 35 U.S.C. 154(b) by 560 days.

(21) Appl. No.: 12/306,021

(22) PCT Filed: Jul. 10, 2007

(86) PCT No.: PCT/DK2007/000351
§ 371 (c)(1),
(2), (4) Date: Dec. 22, 2008

(87) PCT Pub. No.: WO2008/006372
PCT Pub. Date: Jan. 17, 2008

(65) Prior Publication Data
US 2011/0098286 A1 Apr. 28, 2011

Related U.S. Application Data

(60) Provisional application No. 60/819,855, filed on Jul. 10, 2006.

(30) Foreign Application Priority Data

Jul. 10, 2006 (DK) ................................ 2006 00951

(51) Int. Cl.
*C07D 237/30* (2006.01)
*C07D 239/72* (2006.01)
*A61K 31/497* (2006.01)
*A61K 31/517* (2006.01)

(52) U.S. Cl.
USPC ............. 514/266.2; 514/252.02; 544/237; 544/283

(58) Field of Classification Search
None
See application file for complete search history.

(56) References Cited

U.S. PATENT DOCUMENTS

| 2006/0019975 A1* | 1/2006 | Humphrey et al. ...... 514/266.22 |
| 2006/0160814 A1* | 7/2006 | Arrington et al. ............ 514/248 |
| 2007/0265258 A1* | 11/2007 | Liu et al. .................... 514/233.5 |

FOREIGN PATENT DOCUMENTS

| WO | WO 2005/082883 | 9/2005 |
| WO | WO 2006/011040 | 2/2006 |
| WO | WO 2006/028957 | 3/2006 |
| WO | 2007/085954 A2 | 8/2007 |
| WO | WO 2007/085954 | 8/2007 |
| WO | 2007/103370 A2 | 9/2007 |
| WO | 2007/103554 A1 | 9/2007 |
| WO | WO 2007/103370 | 9/2007 |
| WO | WO 2007/103554 | 9/2007 |

OTHER PUBLICATIONS

"Bioisosterism" in the Organic Chemistry of Drug Design and Drug Action by Silverman, Academic Press (London), pp. 19-23 (1991).*
"Bioisosterism: A Rational Approach in Drug Design" by Patani et al., Chem. Rev. 96, 3147-76 (1996).*
"Isosterism and Molecular Modification in Drug Design" by Thornber, Chem. Soc. Rev. 8, 563-80 (1979).*

* cited by examiner

*Primary Examiner* — Brandon Fetterolf
*Assistant Examiner* — Theodore R West
(74) *Attorney, Agent, or Firm* — Kitae T. Lim

(57) ABSTRACT

This invention is directed to compounds, which are PDE10A enzyme inhibitors. The invention provides a pharmaceutical composition comprising a therapeutically effective amount of a compound of the invention and a pharmaceutically acceptable carrier. The present invention also provides a process for the preparation of the compounds of formula I. The present invention further provides a method of treating a subject suffering from a neurodegenerative disorder comprising administering to the subject a therapeutically effective amount of a compound of formula I. The present invention further provides a method of treating a subject suffering from a psychiatric disorder comprising administering to the subject a therapeutically effective amount of a compound of formula I.

14 Claims, No Drawings

(3-ARYL-PIPERAZIN-1-YL), (2-ARYL-MORPHOLIN-4-YL) AND (2-ARYL-THIOMORPHOLIN-4-YL) DERIVATIVES OF 6,7-DIALKOXY-QUINAZOLINE, 6,7-DIALKOXYPHTALAZINE AND 6,7-DIALKOXYISOQUINOLINE AS PDE10A ENZYME INHIBITORS

CROSS-REFERENCE TO RELATED APPLICATION

The present application is a U.S. National Stage Application of International Application No. PCT/DK2007/000351 (International Publication No. WO 2008/006372), filed Jul. 10, 2007, which claims the benefit of Danish Patent Application Serial No. PA 200600951 and U.S. Provisional Patent Application Ser. No. 60/819,855, both of which were filed on Jul. 10, 2006. Each of these applications is herein incorporated by reference in its entirety.

FIELD OF THE INVENTION

The present invention provides for compounds that are PDE10A enzyme inhibitors, and as such are useful to treat associated neurodegenerative and psychiatric disorders. The present invention also provides for pharmaceutical compositions and methods of treating said disorders using the compounds of the invention.

BACKGROUND OF THE INVENTION

Throughout this application, various publications are referenced to in full citations. The disclosures of these publications are hereby incorporated by reference into this application to describe more fully the state of the art to which this invention pertains.

The cyclic nucleotides, cyclic-adenosine monophosphate (cAMP) and cyclic-guanosine monophosphate (cGMP) function as intracellular second messengers regulating a vast array of processes in neurons. Intracellular cAMP and cGMP are generated by adenyl and guanyl cyclases, and are degraded by cyclic nucleotide phosphodiesterases (PDEs). Intracellular levels of cAMP and cGMP are controlled by intracellular signaling, and stimulation/repression of adenyl and guanyl cyclases in response to GPCR activation is a well characterized way of controlling cyclic nucleotide concentrations (Antoni, F. A. *Front. Neuroendocrinol.* 2000, 21(2), 103-132). In neurons, this includes the activation of cAMP and cGMP dependent kinases and subsequent phosphorylation of proteins involved in acute regulation of synaptic transmission as well as in neuronal differentiation and survival.

There are 21 phosphodiesterase genes that can be divided into 11 gene families. There are ten families of adenylyl cyclases, two of guanylyl cyclases, and eleven of phosphodiesterases. PDEs are a class of intracellular enzymes that regulate levels of cAMP and cGMP via hydrolysis of the cyclic nucleotide into their respective nucleotide monophosphates. Some PDEs degrade cAMP, some cGMP and some both. Most PDEs have a relatively widespread expression and have roles in many tissues, while some are more spatially restricted.

Phosphodieasterase 10A (PDE10A) is a dual specificity phosphodiesterase that can convert both cAMP to AMP and cGMP to GMP (Loughney, K. et al. *Gene* 1999, 234, 109-117; Fujishige, K. et al. *Eur. J. Biochem.* 1999, 266, 1118-1127 and Soderling, S. et al. *Proc. Natl. Acad. Sci.* 1999, 96, 7071-7076). PDE10A is primarily expressed in the neurons in the striatum, n. accumbens and in the olfactory tubercle (Kotera, J. et al. *Biochem. Biophys. Res. Comm.* 1999, 261, 551-557 and Seeger, T. F. et al. *Brain Research,* 2003, 985, 113-126).

Mouse PDE10A is the first member of the PDE10 family of phosphodiesterases (Fujishige, K. et al. *J. Biol. Chem.* 1999, 274, 18438-18445 and Loughney, K. et al. *Gene* 1999, 234, 109-117) and N-terminal splice variants of both the rat and human genes have been identified (Kotera, J. et al. *Biochem. Biophys. Res. Comm.* 1999, 261, 551-557 and Fujishige, K. et al. *Eur. J. Biochem.* 1999, 266, 1118-1127). There is a high degree of homology across species. PDE10A is uniquely localized in mammals relative to other PDE families. mRNA for PDE10 is highly expressed in testis and brain (Fujishige, K. et al. *Eur. J. Biochem.* 1999, 266, 1118-1127; Soderling, S. et al. *Proc. Natl. Acad. Sci.* 1999, 96, 7071-7076 and Loughney, K. et al. *Gene* 1999, 234, 109-117). These studies indicate that within the brain, PDE10 expression is highest in the striatum (caudate and putamen), n. accumbens and olfactory tubercle. More recently, an analysis has been made of the expression pattern in rodent brain of PDE10A mRNA (Seeger, T. F. et al. *Abst. Soc. Neurosci.* 2000, 26, 345.10) and PDE10A protein (Menniti, F. S. et al. William Harvey Research Conference 'Phosphodiesterase in Health and Disease', Porto, Portugal, Dec. 5-7, 2001).

PDE10A is expressed at high levels by the medium spiny neurons (MSN) of the caudate n., n. accumbens and the corresponding neurons of the olfactory tubercle. This constitutes the core of the basal ganglia system. The MSN make up a role in a cortical-basal ganglia-thalamocortical loop, integrating convergent cortical/thalamic input, and sending this integrated information back to the cortex. Furthermore, MSN express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. These competing pathways act like the brake and accelerator in a car. In the simplest view, the poverty of movement in Parkinson's disease results from over-activity of the 'indirect' pathway, whereas excess movement in disorders such as Huntington's disease represent over-activity of the direct pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. *Brain Research,* 2003, 985, 113-126).

Dopamine $D_2$ receptor antagonism is well established in the treatment of schizophrenia. Since the 1950's, dopamine $D_2$ receptor antagonism has been the mainstay in psychosis treatment and all effective antipsychotic drugs antagonise $D_2$ receptors. The effects of $D_2$ are likely to be mediated primarily through neurons in the striatum, n. accumbens and olfactory tubercle, since these areas receive the densest dopaminergic projections and have the strongest expression of $D_2$ receptors (Konradi, C. and Heckers, S. *Society of Biological Psychiatry,* 2001, 50, 729-742). Dopamine $D_2$ receptor agonism leads to decrease in cAMP levels in the cells where it is expressed through adenylate cyclase inhibition, and this is a component of $D_2$ signalling (Stoof, J. C. and Kebabian J. W. *Nature* 1981, 294, 366-368 and Neve, K. A. at al. *Journal of Receptors and Signal Transduction* 2004, 24(3), 165-205). Conversely, $D_2$ receptor antagonism effectively increases cAMP levels, and this effect could be mimicked by inhibition of cAMP degrading phosphodiesterases.

Most of the 21 phosphodiesterase genes are widely expressed; therefore inhibition is likely to have side effects. Because PDE10A, in this context, has the desired expression profile with high and relatively specific expression in neurons in striatum, n. accumbens and olfactory tubercle, PDE10A inhibition is likely to have effects similar to $D_2$ receptor antagonism and therefore have antipsychotic effects.

While PDE10A inhibition is expected to mimic $D_2$ receptor antagonism in part, it might be expected to have a different profile. The $D_2$ receptor has signalling components besides cAMP (Neve, K. A. et al. *Journal of Receptors and Signal Transduction* 2004, 24(3), 165-205), wherefore interference with cAMP through PDE10A inhibition may negatively modulate rather than directly antagonise dopamine signaling through $D_2$ receptors. This may reduce the risk of the extrapyrimidal side effects that are seen with strong $D_2$ antagonism. Conversely, PDE10A inhibition may have some effects not seen with $D_2$ receptor antagonism. PDE10A is also expressed in $D_1$ receptors expressing striatal neurons (Seeger, T. F. et al. *Brain Research,* 2003, 985, 113-126). Since $D_1$ receptor agonism leads to stimulation of adenylate cyclase and resulting increase in cAMP levels, PDE10A inhibition is likely to also have effects that mimic $D_1$ receptor agonism. Finally, PDE10A inhibition will not only increase cAMP in cells, but might also be expected to increase cGMP levels, since PDE10A is a dual specificity phosphodiesterase. cGMP activates a number of target protein in cells like cAMP and also interacts with the cAMP signalling pathways. In conclusion, PDE10A inhibition is likely to mimic $D_2$ receptor antagonism in part and therefore has antipsychotic effect, but the profile might differ from that observed with classical $D_2$ receptor antagonists.

The PDE10A inhibitor papaverin is shown to be active in several antipsychotic models. Papaverin potentiated the cataleptic effect of the $D_2$ receptor antagonist haloperidol in rats, but did not cause catalepsy on its own (WO 03/093499). Papaverin reduced hyperactivity in rats induced by PCP, while reduction of amphetamine induced hyperactivity was insignificant (WO 03/093499). These models suggest that PDE10A inhibition has the classic antipsychotic potential that would be expected from theoretical considerations. WO 03/093499 further discloses the use of selective PDE10 inhibitors for the treatment of associated neurologic and psychiatric disorders. Furthermore, PDE10A inhibition reverses subchronic PCP-induced deficits in attentional set-shifting in rats (Rodefer, et al. *Eur. J. Neurosci.* 2005, 4, 1070-1076). This model suggests that PDE10A inhibition might alleviate cognitive deficits associated with schizophrenia.

Accordingly, signal enhancement via elevation of cAMP and cGMP can be induced through the administration of PDE10A inhibitors to treat associated neurological and psychiatric disorders. The PDE10A inhibitors of the present invention are expected to serve as therapies for the treatment of associated neurological and psychiatric disorders and may have the benefit of not possessing unwanted side effects, which are associated with the current therapies on the market.

With respect to inhibitors of PDE10A, EP 1250923 discloses the use of selective PDE10 inhibitors in general, and papaverine in particular, for the treatment of certain neurologic and psychiatric disorders.

WO 05/113517 discloses benzodiazepine stereospecific compounds as inhibitors of phosphodiesterase, especially types 2 and 4, and the prevention and treatment of pathologies involving a central and/or peripheral disorder. WO 02/88096 discloses benzodiazepine derivatives and their uses as inhibitors of phosphodiesterase, especially type 4 in the therapeutic field. WO 04/41258 discloses benzodiazepinone derivatives and their uses as inhibitors of phosphodiesterase, especially type 2 in the therapeutic field.

Pyrrolodihydroisoquinolines and variants thereof are disclosed as inhibitors of PDE10 in WO 05/03129 and WO 05/02579. Piperidinyl-substituted quinazolines and isoquinolines that serve as PDE10 inhibitors are disclosed in WO 05/82883. WO 06/11040 discloses substituted quinazoline and isoquinoline compounds that serve as inhibitors of PDE10. US20050182079 discloses substituted tetrahydroisoquinolinyl derivatives of quinazoline and isoquinoline that serve as effective phosphodiesterase (PDE) inhibitors. In particular, US20050182079 relates to said compounds, which are selective inhibitors of PDE-10. Analogously, US20060019975 discloses piperidine derivatives of quinazoline and isoquinoline that serve as effective phosphodiesterase (PDE) inhibitors. US20060019975 also relates to compounds that are selective inhibitors of PDE10.

WO 06/028957 discloses cinnoline derivatives as inhibitors of phosphodiesterase type 10 for the treatment of psychiatric and neurological syndromes.

However, these disclosures do not pertain to compounds comprising quinazoline, phtalazine or isoquinoline attached to 2-arylpiperazine, 2-arylthiomorpholine or 2-arylmorpholine via a N—C linkage; said compounds having now been found by the inventors to be highly active PDE10A enzyme inhibitors. Such compounds may offer alternatives to current marketed treatments for neurodegenerative and/or psychiatric disorders, which are not efficacious in all patients. Hence, there remains the need for alternative methods of treatment.

SUMMARY OF THE INVENTION

The objective of the present invention is to provide compounds that are PDE10A enzyme inhibitors.

A further objective of the present invention is to provide compounds with such activities which have improved solubility, metabolic stability and/or bioavailability compared to prior art compounds.

Another objective of the invention is to provide an effective treatment, in particular long-term treatment, of a human patient, without causing the side effects typically associated with current therapies for neurologic and psychiatric disorders.

Further objectives of the invention will become apparent upon reading the present specification.

Accordingly, in one aspect the present invention relates to compounds of formula I:

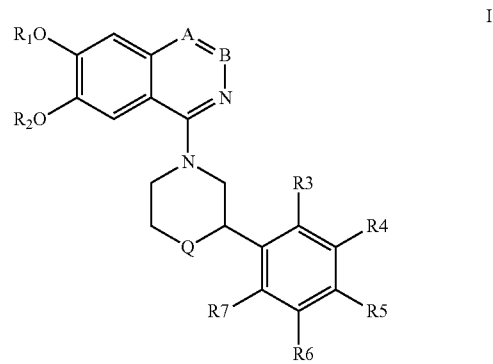

wherein
Q is selected from NH, O or S
A and B are selected independently from CH and N with the proviso that A and B are not both N at the same time
$R_1$ and $R_2$ are independently $C_1$-$C_4$ alkyl
$R_3$, $R_4$, $R_5$, $R_6$ and $R_7$ are independently selected from:
H, ($C_1$-$C_6$) alkyl, ($C_1$-$C_6$) alkoxy, halogen, halo($C_1$-$C_6$) alkyl, ($C_1$-$C_6$)hydroxyalkyl, ($C_1$-$C_6$)alkoxy($C_1$-$C_6$) alkyl, ($C_1$-$C_6$)hydroxycycloalkyl, ($C_3$-$C_8$)cycloalkoxy, ($C_1$-$C_6$)alkoxy($C_3$-$C_8$)cycloalkyl, heterocycloalkyl, hydroxyheterocycloalkyl, and ($C_1$-$C_6$)alkoxy-heterocycloalkyl, wherein each ($C_3$-$C_8$) cycloalkyl or heterocycloalkyl moiety may be independently substituted with from one to three ($C_1$-$C_6$) alkyl;
a —$NR_8R_9$ group, wherein $R_8$ and $R_9$ are independently selected from hydrogen, $C_1$-$C_6$ alkyl, halo($C_1$-$C_6$) alkyl, ($C_3$-$C_8$)cycloalkyl, heterocycloalkyl;
a 6-7-membered aliphatic heterocycle:

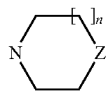

wherein n is 1 or 2 and Z is oxygen or $NR_{10}$, wherein $R_{10}$ is hydrogen or ($C_1$-$C_6$) alkyl, or
a ketone, sulfone, ester, amide, sulfonic ester or sulfonamide, selected from

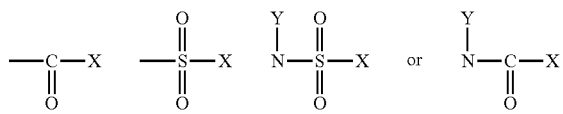

wherein Y is hydrogen or ($C_1$-$C_6$) alkyl and X is a selected from:
a ($C_1$-$C_6$) alkyl group unsubstituted or substituted with one or more halogens,
—O—($C_1$-$C_6$) alkyl unsubstituted or substituted with one or more halogens,
a —$NR_{11}R_{12}$ group, where $R_{11}$ and $R_{12}$ are independently selected from hydrogen, $C_1$-$C_6$ alkyl, halo($C_1$-$C_6$)alkyl, ($C_3$-$C_8$)cycloalkyl, heterocycloalkyl, or
a 6-7-membered aliphatic heterocycle:

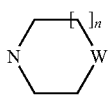

wherein n is 1 or 2; and W is oxygen or $NR_{13}$, wherein $R_{13}$ is hydrogen or ($C_1$-$C_6$) alkyl, or
two adjacent substituents selected from $R_3$, $R_4$, $R_5$, $R_6$ and $R_7$ may together with the aromatic ring they are attached to form a 5-7 membered, saturated or unsaturated ring containing carbon and one or two heteroatoms selected from N, O or S, and optionally substituted with an ($C_1$-$C_6$) alkoxy group. The remaining three substituents selected from $R_3$, $R_4$, $R_5$, $R_6$ and $R_7$, which do not take part of the ring, are independently selected as stated above.
or a pharmaceutically acceptable salt thereof.

In a particular embodiment, the invention relates to compounds of formula I in the form of a single enantiomer, a single diastereomer, a mixture of enantiomers, a mixture of diastereomers, or a polymorph.

In separate embodiments of the invention, the compound is selected from one of the specific compounds disclosed in the Experimental Section.

The invention provides a compound of formula I, or a pharmaceutically acceptable acid addition salt thereof, for use as a medicament.

In another aspect the present invention provides a pharmaceutical composition comprising a therapeutically effective amount of a compound of formula I and a pharmaceutically acceptable carrier or diluent.

The invention further provides the use of a compound of formula I, or a pharmaceutically acceptable acid addition salt thereof, for the preparation of a medicament for the treatment of neurodegenerative or psychiatric disorders.

Furthermore, in yet another aspect the present invention provides a method of treating a subject suffering from a neurodegenerative disorder comprising administering to the subject a therapeutically effective amount of a compound of formula I. In a still further aspect the present invention provides a method of treating a subject suffering from a psychiatric disorder comprising administering to the subject a therapeutically effective amount of a compound of formula I.

DETAILED DESCRIPTION OF THE INVENTION

Definition of Substitutents

As used in the present invention, the terms "halo" and "halogen" are used interchangeably and refer to fluorine, chlorine, bromine or iodine.

Furthermore, the term "$C_1$-$C_6$ alkyl" refers to a straight chained or branched saturated hydrocarbon having from one to six carbon atoms inclusive. Examples of such groups include, but are not limited to, methyl, 2-propyl, 1-butyl, 2-butyl, 2-methyl-2-propyl, 2-methyl-1-butyl and n-hexyl. Similarly, the term "$C_1$-$C_4$ alkyl" refers to a straight chained or branched saturated hydrocarbon having from one to four carbon atoms inclusive. The expression "$C_1$-$C_6$ hydroxyalkyl" refers to a $C_1$-$C_6$ alkyl group as defined above, which is substituted with one hydroxy group. The term "halo($C_1$-$C_6$) alkyl" refers to a $C_1$-$C_6$ alkyl group as defined above, which is substituted with up to three halogen atoms.

The expression "$C_1$-$C_6$ alkoxy" refers to a straight chain or branched saturated alkoxy group having from one to six carbon atoms inclusive with the open valency on the oxygen. Examples of such groups include, but are not limited to, methoxy, ethoxy, n-butoxy, 2-methyl-pentoxy and n-hexyloxy. The term "halo($C_1$-$C_6$)alkoxy" refers to a $C_1$-$C_6$ alkoxy group as defined above, which is substituted with up to three halogen atoms. The term "$C_1$-$C_6$ alkoxy($C_1$-$C_6$)alkyl" refers to a $C_1$-$C_6$ alkyl group as defined above, which is substituted with a $C_1$-$C_6$ alkoxy group as defined above.

The term "$C_3$-$C_8$ cycloalkyl" typically refers to cyclopropyl, cyclobutyl, cyclopentyl, cyclohexyl, cycloheptyl and cyclooctyl. The term "$C_3$-$C_8$ hydroxycycloalkyl" refers to $C_3$-$C_8$ cycloalkyl as defined above, which is substituted with one hydroxy group. The expression "$C_1$-$C_6$ alkoxy($C_3$-$C_8$) cycloalkyl" refers to a $C_3$-$C_8$ cycloalkyl as defined above, which is substituted with a straight chained or branched $C_1$-$C_6$ alkoxy. The term "$C_3$-$C_8$ cycloalkoxy" typically refers to cyclopropyloxy, cyclobutyloxy, cyclopentyloxy, cyclohexyloxy, cycloheptoxy and cyclooctoxy in which the open valency is on the oxygen atom.

The term "heterocycloalkyl" refers to a four to eight membered ring containing carbon atoms and up to three N, O or S atoms provided that the four to eight membered ring does not contain adjacent O or adjacent S atoms. The open valency is on either the heteroatom or carbon atom. Examples of such groups include, but are not limited to, azetidinyl, oxetanyl, piperazinyl, morpholinyl, thiomorpholinyl and [1,4]diazepanyl. The term "hydroxyheterocycloalkyl" refers to a heterocycloalkyl as defined above, which is substituted with one hydroxy group. The term "$C_1$-$C_6$ alkoxy-heterocycloalkyl" refers to a heterocycloalkyl as defined above, which is substituted with a $C_1$-$C_6$ alkoxy group.

Additionally, the present invention further provides for certain embodiments of the invention, which are described below.

Formula I defines the compounds of the present invention by the ring variables A, B and Q, and by the substituents $R_1$, $R_2$, $R_3$, $R_4$, $R_5$, $R_6$ and $R_7$.

For each of the following 9 combinations of ring variables the present invention further comprise individual embodiments of the compounds of Formula I:

| A = | B = | Q = |
| --- | --- | --- |
| CH | N | NH |
| CH | CH | NH |
| N | CH | NH |
| CH | N | O |
| CH | CH | O |
| N | CH | O |
| CH | N | S |
| CH | CH | S |
| N | CH | S |

In a preferred embodiment of the invention, Q=NH

In one embodiment $R_1$ and $R_2$ are independently $C_1$-$C_2$ alkyl, such as methyl. Typically, R1 and $R_2$ are both methyl In one embodiment, $R_3$ is selected from hydrogen, ($C_1$-$C_6$) alkoxy or halogen, such as hydrogen, methoxy, chlorine and bromine; or a carboxamide or sulfonamide selected from:

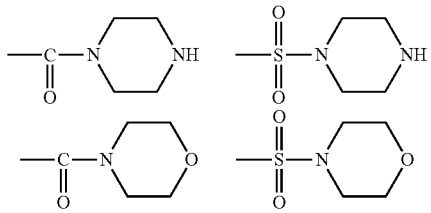

Typically $R_3$ is hydrogen.

In another embodiment of the invention, $R_4$ is selected from hydrogen, ($C_1$-$C_6$) alkoxy, halogen or nitro such as hydrogen, methoxy, chlorine, bromine and nitro, or a carboxamide or sulfonamide selected from:

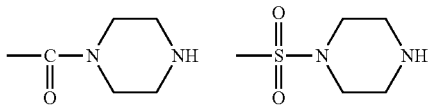

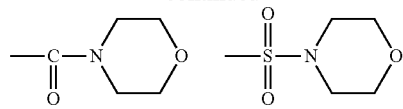

Typically $R_4$ is hydrogen or methoxy.

In yet another embodiment $R_5$ is selected from:
H, ($C_1$-$C_6$) alkyl, ($C_1$-$C_6$) alkoxy, halogen, halo($C_1$-$C_6$) alkyl, nitro or
an amino group —$NR_8R_9$, where $R_8$ and $R_9$ are independently selected from hydrogen, $C_1$-$C_6$ alkyl, halo($C_1$-$C_6$)alkyl, ($C_3$-$C_8$)cycloalkyl, heterocycloalkyl, or
a 6-7-membered aliphatic heterocycle:

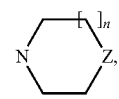

wherein n is 1 or 2 and Z is oxygen or $NR_{10}$, wherein $R_{10}$ is hydrogen or ($C_1$-$C_6$) alkyl, or a carboxamide or sulfonamide selected from:

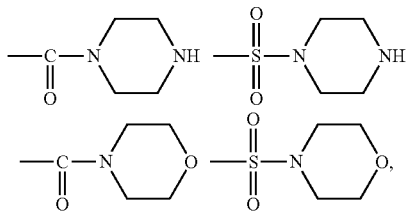

such as hydrogen, methyl, ethyl, methoxy, fluorine, chlorine, bromine, trifluoromethyl, nitro, dimethylamino, morpholino. Typically $R_5$ is hydrogen, methyl, dimethylamino, methoxy fluorine, chlorine or trifluoromethyl.

In another embodiment, $R_6$ is selected from hydrogen, ($C_1$-$C_6$) alkoxy, halogen or nitro such as hydrogen, methoxy, chlorine, bromine and nitro, or a carboxamide or sulfonamide selected from:

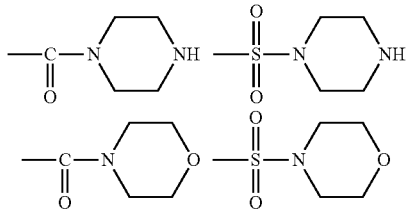

Typically $R_6$ is hydrogen or methoxy.

In one embodiment, $R_7$ is selected from hydrogen, ($C_1$-$C_6$) alkoxy or halogen, such as hydrogen, methoxy, chlorine and bromine; or a carboxamide or sulfonamide selected from:

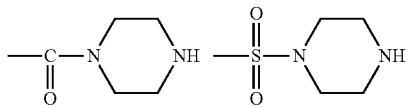

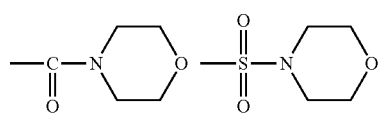

Typically $R_7$ is hydrogen.

In another embodiment two adjacent substituents selected from $R_3$, $R_4$, $R_5$, $R_6$ and $R_7$ may, together with the aromatic ring they are attached to, form a 5-7 membered, saturated or unsaturated ring, optionally containing one or two heteroatoms selected from N, O or S, such as a five-membered ring containing two oxygen atoms, or a six-membered ring containing only carbon atoms.

In a further embodiment, two to five of $R_3$, $R_4$, $R_5$, $R_6$ and $R_7$ are H. Typically three to four of $R_3$, $R_4$, $R_5$, $R_6$ and $R_7$ are H.

In a preferred embodiment one to three of $R_4$, $R_5$ or $R_6$ are electron-donating substituents such as ($C_1$-$C_6$) alkoxy, ($C_1$-$C_6$) alkyl or —$NR_8R_9$, where $R_8$ and $R_9$ are independently selected from hydrogen, $C_1$-$C_6$ alkyl, halo($C_1$-$C_6$)alkyl, ($C_3$-$C_8$)cycloalkyl, heterocycloalkyl, such as methoxy, methyl, ethyl, dimethylamino and morpholino.

In another embodiment two adjacent substituents selected from $R_3$, $R_4$, $R_5$, $R_6$ and $R_7$ may, together with the aromatic ring they are attached to, form a 5 membered, saturated ring containing two oxygen atoms:

In yet another embodiment two adjacent substituents selected from $R_3$, $R_4$, $R_5$, $R_6$ and $R_7$ may, together with the aromatic ring they are attached to, form a 6 membered aromatic ring:

or pharmaceutically acceptable salts thereof.

Another aspect of the present invention is a process for the preparation of the compounds of Formula I comprising reacting a compound of Formula II:

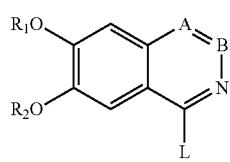

in which L is a leaving group selected from Cl, Br, I, $OSO_2CF_3$, and A, B, $R_1$ and $R_2$ are as defined above; with a compound of Formula III:

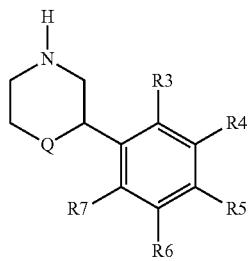

either as the free base or an addition salt hereof; wherein Q, $R_3$, $R_4$, $R_5$, $R_6$ and $R_7$ are as defined above; either neat, or in an inert solvent or mixture of solvents, at a temperature between 0 to about 200° C., optionally in the presence of a base, followed by work-up and isolation of the product of Formula I, either as its free base or as an acid addition salt hereof.

In an embodiment of the present invention the solvent used for the preparation of the compounds of Formula I is toluene or mixtures of toluene with a protic solvent such as 2-propanol, preferably a 1:1 mixture of toluene and 2-propanol.

In another embodiment of the present invention the base used for the preparation of the compounds of Formula I is potassium carbonate.

In yet another embodiment of the present invention the preferred reaction temperature used for the preparation of the compounds of Formula I is 180° C.

In a further embodiment the process for the preparation of the compounds of Formula I comprising reacting a compound of Formula II with a compound of Formula III in the presence of an alkoxide base, such as sodium tert-butoxide, and a palladium catalyst prepared in situ by mixing a palladium (II) source such as $Pd(OAc)_2$ or $Pd_2(dba)_3$ with a bisphosphine ligand such as BINAP (i.e. 2,2'-bis(diphenylphosphino)-1,1'-binaphthyl), in a convenient reaction solvent such as toluene, followed by heating the reaction mixture at 50-150° C. for 3-12 hours, typically for 7 hours at 100° C.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like.

Further examples of pharmaceutically acceptable inorganic or organic acid addition salts include the pharmaceutically acceptable salts listed in Berge, S. M. et al., *J. Pharma. Sci.* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Racemic forms may be resolved into the optical antipodes by known methods, for example, by separation of diastereomeric salts thereof with an optically active acid, and liberating the optically active amine compound by treatment with a base. Separation of such diastereomeric salts can be achieved, e.g. by fractional crystallization. The optically active acids suitable for this purpose may include, but are not limited to d- or l-tartaric, mandelic or camphorsulfonic acids. Another method for resolving racemates into the optical antipodes is based upon chromatography on an optically active matrix. The compounds of the present invention may also be resolved by the formation and separation, e.g. chromatographic separation, of diastereomeric derivatives from chiral derivatizing reagents, such as a chiral alkylating or acylating reagents, followed by cleavage of the chiral auxiliary.

Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York 1981. Optically active compounds were also be prepared from optically active starting materials.

Pharmaceutical Compositions

The present invention further provides a pharmaceutical composition comprising a therapeutically effective amount of a compound of formula I and a pharmaceutically acceptable carrier or diluent. The present invention also provides a pharmaceutical composition comprising a therapeutically effective amount of one of the specific compounds disclosed in the Experimental Section and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of formula I and at least one pharmaceutically acceptable carrier or diluent. In an embodiment of the present invention, the compound utilized in the aforementioned process is one of the specific compounds disclosed in the Experimental Section.

The compounds of this invention are generally utilized as the free substance or as a pharmaceutically acceptable salt thereof. One example is an acid addition salt of a compound having the utility of a free base. When a compound of formula I contains a free base such salts are prepared in a conventional manner by treating a solution or suspension of a free base of formula I with a molar equivalent of a pharmaceutically acceptable acid. Representative examples of suitable organic and inorganic acids are described above.

For parenteral administration, solutions of the compounds of formula I in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula I may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula I and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatine, lactose, gums, and the like. Any other adjuvants or additives usually used for such purposes such as colorings, flavorings, preservatives etc. may be used provided that they are compatible with the active ingredients.

Treatment of Disorders

As mentioned above, the compounds of formula I are PDE10A enzyme inhibitors and as such are useful to treat associated neurological and psychiatric disorders. The present invention provides a method of treating a subject suffering from a neurodegenerative disorder selected from a cognition disorder or movement disorder which comprises administering to the subject a therapeutically effective amount of a compound of formula I.

This invention also provides a method of treating a subject suffering from a psychiatric disorder, which comprises administering to the subject a therapeutically effective amount of a compound of formula I. Examples of psychiatric disorders that can be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, *cannabis*, cocaine, hallucinogens, inhalants, opioids, or phencyclidine; personality disorder of the paranoid type; and personality disorder of the schizoid type; and the anxiety disorder is selected from panic disorder; agoraphobia; a specific phobia; social phobia; obsessive-compulsive disorder; post-traumatic stress disorder; acute stress disorder; and generalized anxiety disorder.

The present invention provides a method of treating a subject suffering from a cognition disorder, which comprises administering to the subject a therapeutically effective amount of a compound of formula I. Examples of cognition disorders that can be treated according to the present invention include, but are not limited to, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

This invention also provides a method of treating a movement disorder, which comprises administering to the subject a therapeutically effective amount of a compound of formula I. Examples of movement disorders that can be treated according to the present invention include, but are not limited to, Huntington's disease and dyskinesia associated with dopamine agonist therapy. This invention further provides a method of treating a movement disorder selected from Parkinson's disease and restless leg syndrome, which comprises administering to the subject a therapeutically effective amount of a compound of formula I.

This invention also provides a method of treating a mood disorder, which comprises administering to the subject a therapeutically effective amount of a compound of formula I. Examples of mood disorders and mood episodes that can be treated according to the present invention include, but are not limited to, major depressive episode of the mild, moderate or severe type, a manic or mixed mood episode, a hypomanic mood episode; a depressive episode with a typical features; a depressive episode with melancholic features; a depressive episode with catatonic features; a mood episode with post-partum onset; post-stroke depression; major depressive disorder; dysthymic disorder; minor depressive disorder; pre-menstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder. It is understood that a mood disorder is a psychiatric disorder.

The invention also provides the use of a compound of formula I or a pharmaceutically acceptable acid addition salt thereof for the preparation of a medicament for the treatment of neurodegenerative or psychiatric disorders wherein the neurodegenerative disorder is selected from the group consisting of Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline, and wherein the psychiatric disorder is selected from the group consisting of schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, *cannabis*, cocaine, hallucinogens, inhalants, opioids, or phencyclidine; personality disorder of the paranoid type; and personality disorder of the schizoid type.

The present invention will be better understood from the Experimental Section that follows. However, one skilled in the art will readily appreciate that the specific methods and results discussed therein are merely illustrative of the invention as described more fully in the claims that follow thereafter.

Experimental Section

General Methods

Analytical LC-MS data were obtained on a PE Sciex API 150EX instrument equipped with atmospheric pressure photo ionisation and a Shimadzu LC-8A/SLC-10A LC system. Column: 30×4.6 mm Waters Symmetry C18 column with 3.5 μm particle size; Solvent system: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. Purity was determined by integration of the UV (254 nm) and ELSD trace. The retention times ($t_R$) are expressed in minutes.

Preparative LC-MS-purification was performed on the same instrument with atmospheric pressure chemical ionisation. Column: 50×20 mm YMC ODS-A with 5 μm particle size; Method: Linear gradient elution with 80% A to 100% B in 7 minutes and with a flow rate of 22.7 mL/minute. Fraction collection was performed by split-flow MS detection.

Preparation of the Compounds of the Invention

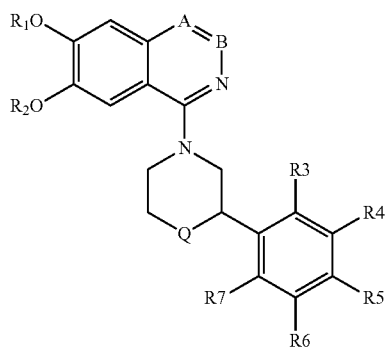

Compounds of the general formula I of the invention may be prepared as described in the following reaction schemes. Unless otherwise indicated, in the reaction schemes and discussion that follow, $R_1$-$R_7$, A, B, Q, L, X, Y, Z and n are as defined above. Scheme 1 below depicts a coupling reaction between a compound of formula II and a derivative of 2-arylpiperazine, 2-arylthiomorpholine or 2-arylmorpholine of formula III, to generate the dialkoxy substituted compounds of formula I.

Scheme 1

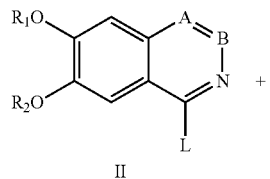

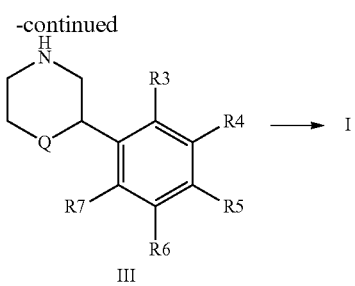

This reaction is typically carried out in a solvent such as, for example, toluene, optionally in the presence of a carbonate base, at a temperature range of from about 0° C. to about 200° C. Other suitable solvents include benzene, chloroform, dioxane, ethyl acetate, 2-propanol and xylene. Alternatively, solvent mixtures such as toluene/2-propanol can be used. Preferably the reactants are heated under reflux in a solvent mixture of toluene and 2-propanol for a period of from about 2 hours to about 24 hours, optionally using a microwave oven.

The reaction depicted in Scheme 1 can also conveniently be carried out in a palladium-catalyzed fashion. Typically, a mixture of a compound of formula II, a compound of formula III and a palladium (II) source such as $Pd(OAc)_2$ or $Pd_2(dba)_3$ is heated in a convenient solvent such as toluene in the presence of a bisphosphine ligand, such as 2,2'-bis(diphenylphosphino)-1,1'-binaphthyl "BINAP", and an alkoxide base such as sodium tert-butoxide. The reaction mixture is stirred at 100° C. for 7 hr, followed by purification of the product by preparative HPLC to obtain the desired product.

The prepared compounds all display a satisfactory aqueous solubility. However, the piperazine derivatives (Formula I, Q=NH) appear in general to be significantly better soluble than the analogous morpholine- or thimorpholine derivatives (Formula I, Q=O or S, respectively).

Starting materials of formula II where A=nitrogen and B=Carbon i.e. quinazolines are either commercially available or can be prepared as described in the literature e.g. PC Int. Appl. 2003008388, 30 Jan. 2003; US__20060019975_A1 and Wright, S. W., et al., J. Med. Chem., 2002. 45: p. 3865-3877.

Starting materials of formula II where A=Carbon and B=Nitrogen i.e. phtalazines and starting materials of formula II where A=B=Carbon i.e. isoquinolines are either commercially available or can be prepared as described in the literature e.g. J. Med. Chem. 1999, 42, 3860-3873, Weinstock, J. Org. Chem. 26, 3511 (1961); F. Elou and A. Deryckere, Helv. Chim. Acta 52, 1755 (1969); Patent; Pfizer Inc.; Publ.: U.S. Pat. No. 4,370,328 A1 (1983/01/25), Appl.: US1980-170777 (1980/07/21).

Starting materials of formula III are either commercially available or can be prepared as described in the literature e.g. Wolters, R. J. et al.; J. Pharm. Sci.; 63; 1974; 1379-1382, Busch, N. et al.; Eur. J. Med. Chem. Chim. Ther.; 11; 1976; 201-207, Ruano, J. L. et al. J. Org. Chem.; 57; 15; 1992; 4215-4224, J. Med. Chem. 1983, 26, p 254; Ref. Patent; Hokuriku Pharm.; DE 2718451; 1977; Chem. Abstr.; EN; 88; 89714; Blythin et al. Bioorg. Med. Chem. Lett. 2002, 12, 3161.

The starting material of formula III may also be produced following the procedure below: A stirred mixture of 0.03 eq of $Pd(OAc)_2$ and 0.04 eq of 1,1-bis(diphenylphosphino) ferrocene(dppf) in dimethylformamide was heated at 50° C. for 0.25 h. After cooling, 1 eq of the 2-chloro-pyrazine, 1.1 eq of the areneboronec acid, and 1.4 eq of $Et_3N$ were added, and the mixture was stirred at 90° C. for 12 h. After cooling, the black mixture was concentrated to dryness on the evaporator, and the product was taken up in 50 mL of chloroform, washed with 25 mL of dilute NH₄OH solution, and concentrated to dryness. The residue was purified on flash chromatography to give the pure product of formula III.

The invention disclosed herein is further illustrated by the following non-limiting examples.

Example 1

1. 6,7-Dimethoxy-4-(2-phenyl-thiomorpholin-4-yl)-quinazoline

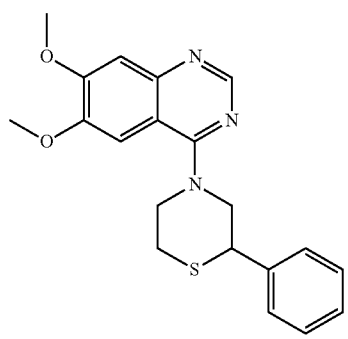 [SMILES: COc1cc2ncnc(N3CCSC(c4ccccc4)C3)c2cc1OC]

2-Phenyl-thiomorpholine (1 mole equivalent), 4-Chloro-6,7-dimethoxy-quinazoline (1 mole equivalent) and potassium carbonate (1 mole equivalent) were added to a 1:1 mixture of toluene and 2-propanol, corresponding to a final concentration of about 0.5 molar. The reaction mixture was heated in a microwave oven at 180° C. for 15 minutes, and filtrated. The solvent was removed under vacuum and the resultant solid was subjected to preparative LC-MS-purification. Fractions containing the product were collected, pooled and evaporated in vacuo to give the product.

The following compounds were prepared analogously:

2. 6,7-Dimethoxy-4-(3-(3-methoxyphenyl)-piperazin-1-yl)-quinazoline

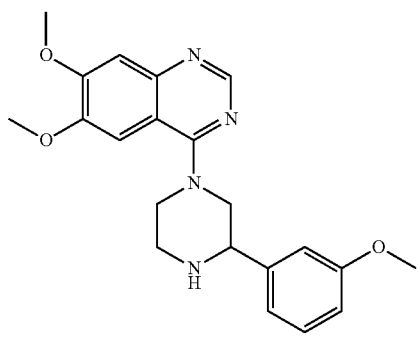

The title compound was prepared from 2-(3-methoxyphenyl)-piperazine and 4-Chloro-6,7-dimethoxy-quinazoline 3. 6,7-Dimethoxy-4-(2-(4-methylphenyl)-morpholin-4-yl)-quinazoline

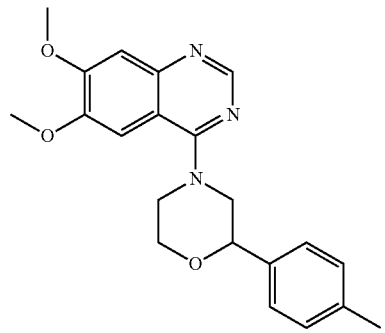

The title compound was prepared from 2-(4-methylphenyl)-morpholine and 4-Chloro-6,7-dimethoxy-quinazoline 4. 6,7-Dimethoxy-4-((R)-3-(3-methoxyphenyl)-piperazin-1-yl)-quinazoline

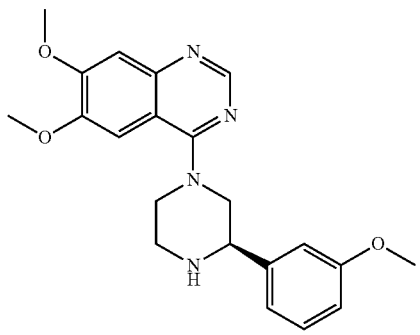

The title compound was prepared from (R)-2-(3-methoxyphenyl)-piperazine and 4-Chloro-6,7-dimethoxy-quinazoline 5. 6,7-Dimethoxy-4-((S)-3-(3-methoxyphenyl)-piperazin-1-yl)-quinazoline

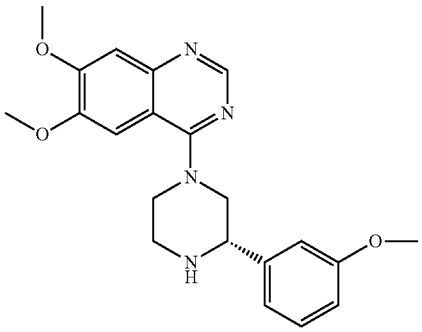

The title compound was prepared from (S)-2-(3-methoxyphenyl)-piperazine and 4-Chloro-6,7-dimethoxy-quinazoline 6,7-Dimethoxy-4-((R)-3-phenyl-piperazin-1-yl)-quinazoline

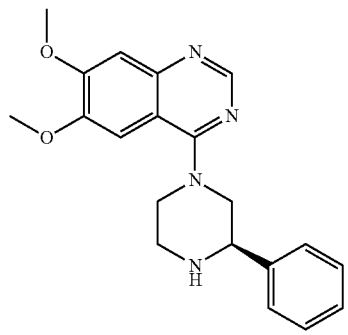 [SMILES: COc1cc2ncnc(N3CCN[C@H](c4ccccc4)C3)c2cc1OC]

The title compound was prepared from (R)-2-phenyl-piperazine and 4-Chloro-6,7-dimethoxy-quinazoline 6. 6,7-Dimethoxy-4-((S)-3-phenyl-piperazin-1-yl)-quinazoline

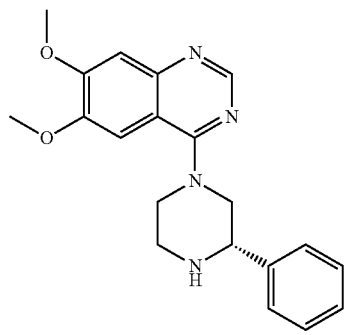 [SMILES: COc1cc2ncnc(N3CCN[C@@H](c4ccccc4)C3)c2cc1OC]

The title compound was prepared from (S)-2-phenyl-piperazine and 4-Chloro-6,7-dimethoxy-quinazoline 7. 4-[3-(3,4,5-trimethoxyphenyl)-piperazin-1-yl]-6,7-dimethoxy-quinazoline

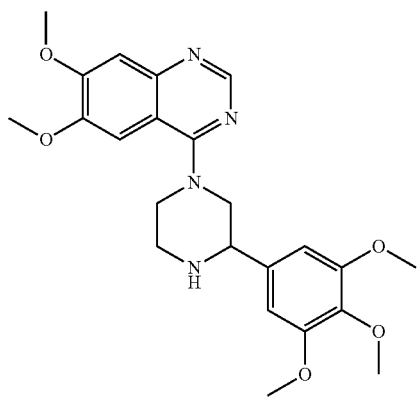

The title compound was prepared from 2-(3,4,5-trimethoxyphenyl)-piperazine and 4-Chloro-6,7-dimethoxy-quinazoline 8. 4-[3-(2-methoxyphenyl)-piperazin-1-yl]-6,7-dimethoxy-quinazoline

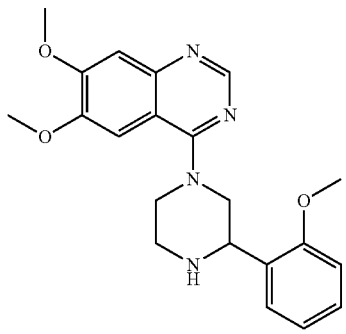

The title compound was prepared from 2-(2-methoxyphenyl)-piperazine and 4-Chloro-6,7-dimethoxy-quinazoline 9. 6,7-Dimethoxy-4-(2-(4-fluorophenyl)-morpholin-4-yl)-quinazoline

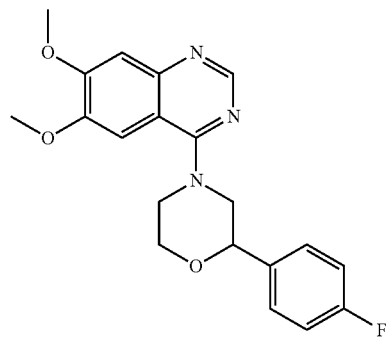 [SMILES: COc1cc2ncnc(N3CCOC(c4ccc(F)cc4)C3)c2cc1OC]

The title compound was prepared from 2-(4-fluorophenyl)-morpholine and 4-Chloro-6,7-dimethoxy-quinazoline 10. 6,7-Dimethoxy-4-(2-(4-chlorophenyl)-morpholin-4-yl)-quinazoline

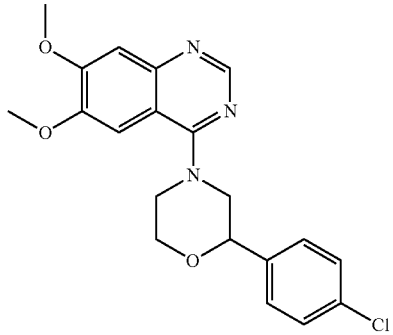

The title compound was prepared from 2-(4-chlorophenyl)-morpholine and 4-Chloro-6,7-dimethoxy-quinazoline 11. 6,7-Dimethoxy-4-(2-(4-trifluomethylphenyl)-morpholin-4-yl)-quinazoline

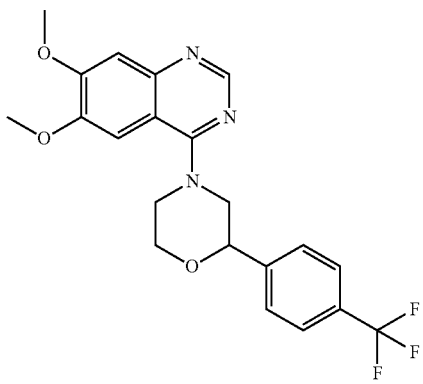 [SMILES: COc1cc2ncnc(N3CCOC(c4ccc(C(F)(F)F)cc4)C3)c2cc1OC]

The title compound was prepared from 2-(4-trifluorophenyl)-morpholine and 4-Chloro-6,7-dimethoxy-quinazoline 12. 6,7-Dimethoxy-4-(2-(2-chlorophenyl)-morpholin-4-yl)-quinazoline

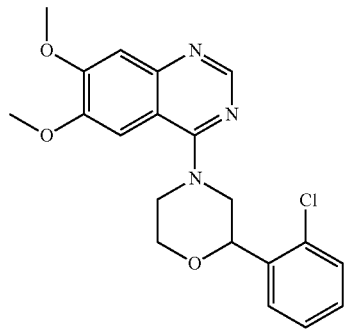 [SMILES: COc1cc2ncnc(N3CCOC(c4ccccc4Cl)C3)c2cc1OC]

The title compound was prepared from 2-(2-chlorophenyl)-morpholine and 4-Chloro-6,7-dimethoxy-quinazoline 13. 4-[3-(4-dimethylaminophenyl)-piperazin-1-yl]-6,7-dimethoxy-quinazoline

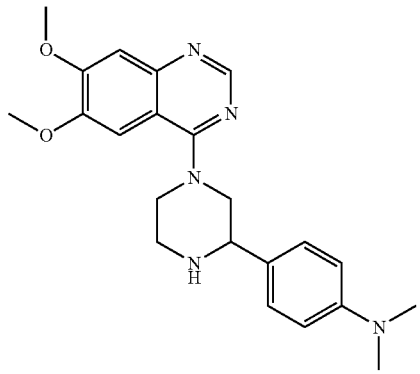

The title compound was prepared from 2-(4-dimethylaminophenyl)-piperazine and 4-Chloro-6,7-dimethoxy-quinazoline 14. 4-[3-(3,4-methylenedioxyphenyl)-piperazin-1-yl]-6,7-dimethoxy-quinazoline

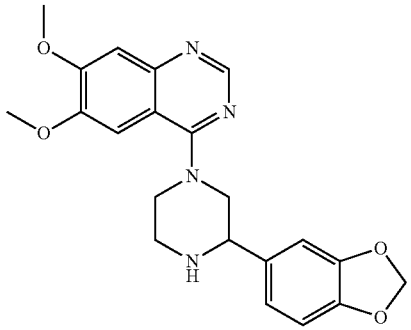 [SMILES: COc1cc2ncnc(N3CCNC(c4ccc5c(c4)OCO5)C3)c2cc1OC]

The title compound was prepared from 2-(3,4-methylenedioxyphenyl)-piperazine and 4-Chloro-6,7-dimethoxy-quinazoline 15. 4-[3-(2,5-dichlorophenyl)-piperazin-1-yl]-6,7-dimethoxy-quinazoline

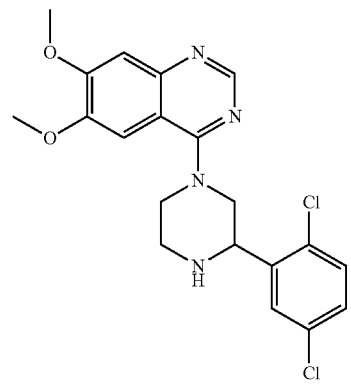 [SMILES: COc1cc2ncnc(N3CCNC(c4cc(Cl)ccc4Cl)C3)c2cc1OC]

The title compound was prepared from 2-(2,5-dichlorophenyl)-piperazine and 4-Chloro-6,7-dimethoxy-quinazoline 16. 4-[3-(2,5-dichlorophenyl)-piperazin-1-yl]-6,7-dimethoxy-quinazoline

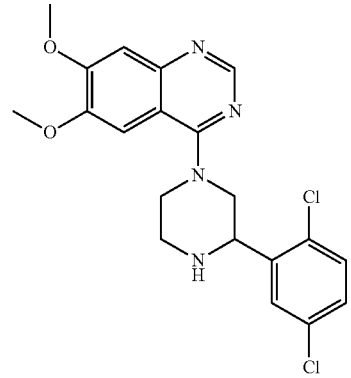 [SMILES: COc1cc2ncnc(N3CCNC(c4cc(Cl)ccc4Cl)C3)c2cc1OC]

The title compound was prepared from 2-(2,5-dichlorophenyl)-piperazine and 4-Chloro-6,7-dimethoxy-quinazoline The following compounds can be prepared analogously:

17. 4-[3-(2,5-dichloro-phenyl)-piperazin-1-yl]-6,7-dimethoxy-quinazoline

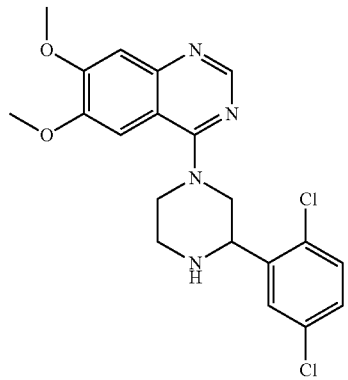 [SMILES: COc1cc2ncnc(N3CCNC(c4cc(Cl)ccc4Cl)C3)c2cc1OC]

The title compound was prepared from 2-(2,5-dichlorophenyl)-piperazine and 4-Chloro-6,7-dimethoxy-quinazoline 18. 4-[3-(4-methylphenyl)-piperazin-1-yl]-6,7-dimethoxy-quinazoline

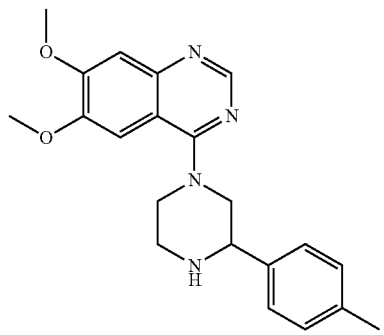

The title compound was prepared from 2-(4-methylphenyl)-piperazine and 4-Chloro-6,7-dimethoxy-quinazoline 19. 4-[3-(4-fluorophenyl)-piperazin-1-yl]-6,7-dimethoxy-quinazoline

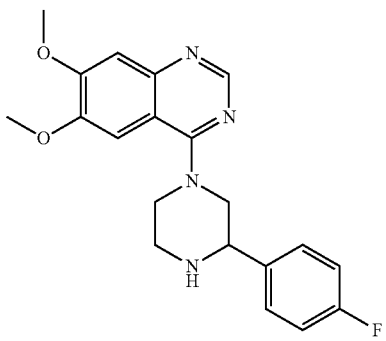 [SMILES: COc1cc2ncnc(N3CCNC(c4ccc(F)cc4)C3)c2cc1OC]

The title compound was prepared from 2-(4-fluorophenyl)-piperazine and 4-Chloro-6,7-dimethoxy-quinazoline 20. 4-[3-(4-ethylphenyl)-piperazin-1-yl]-6,7-dimethoxy-quinazoline

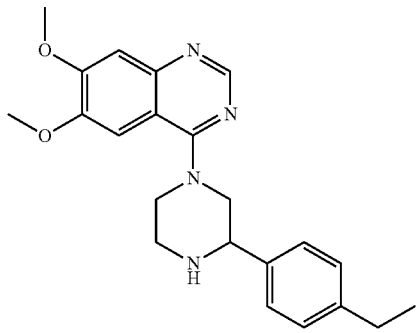 [SMILES: CCc1ccc(C2CN(c3ncnc4cc(OC)c(OC)cc34)CCN2)cc1]

The title compound was prepared from 2-(4-ethylphenyl)-piperazine and 4-Chloro-6,7-dimethoxy-quinazoline 21. 4-[3-(4-methoxyphenyl)-piperazin-1-yl]-6,7-dimethoxy-quinazoline

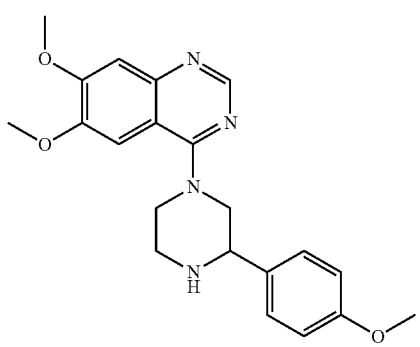

The title compound was prepared from 2-(4-methoxyphenyl)-piperazine and 4-Chloro-6,7-dimethoxy-quinazoline 22. 4-[3-(3-chlorophenyl)-piperazin-1-yl]-6,7-dimethoxy-quinazoline

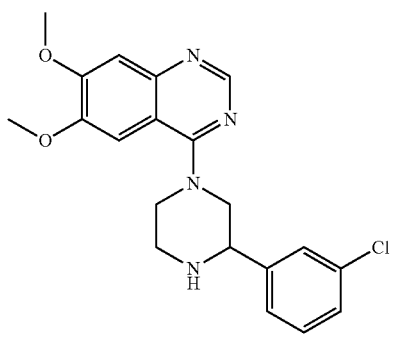 [SMILES: COc1cc2ncnc(N3CCNC(c4cccc(Cl)c4)C3)c2cc1OC]

The title compound was prepared from 2-(3-chlorophenyl)-piperazine and 4-Chloro-6,7-dimethoxy-quinazoline 23. 4-[3-(4-chlorophenyl)-piperazin-1-yl]-6,7-dimethoxy-quinazoline

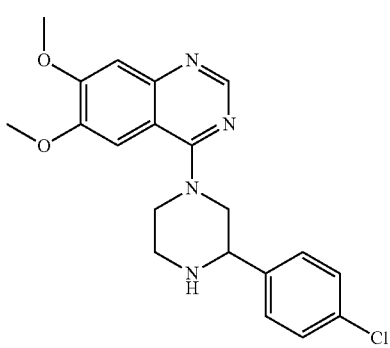 [SMILES: COc1cc2ncnc(N3CCNC(c4ccc(Cl)cc4)C3)c2cc1OC]

The title compound is prepared from 2-(4-chlorophenyl)-piperazine and 4-Chloro-6,7-dimethoxy-quinazoline 24. 4-[3-(3-nitrophenyl)-piperazin-1-yl]-6,7-dimethoxy-quinazoline

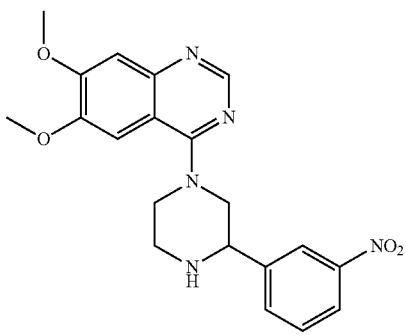 [SMILES: COc1cc2ncnc(N3CCNC(c4cccc([N+](=O)[O-])c4)C3)c2cc1OC]

The title compound was prepared from 2-(3-nitrophenyl)-piperazine and 4-Chloro-6,7-dimethoxy-quinazoline
25. 4-[3-(4-nitrophenyl)-piperazin-1-yl]-6,7-dimethoxy-quinazoline 25. 4-[3-(4-nitrophenyl)-piperazin-1-yl]-6,7-dimethoxy-quinazoline

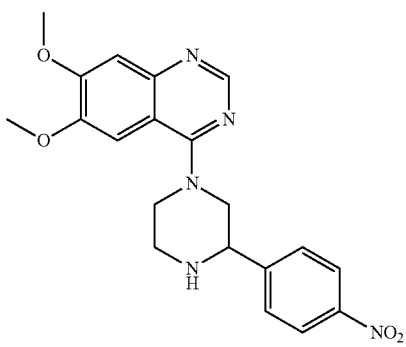 [SMILES: COc1cc2ncnc(N3CCNC(c4ccc([N+](=O)[O-])cc4)C3)c2cc1OC]

The title compound is prepared from 2-(4-nitrophenyl)-piperazine and 4-Chloro-6,7-dimethoxy-quinazoline 26. 6,7-Dimethoxy-4-(3-naphthalen-2-yl-piperazin-1-yl)-quinazoline

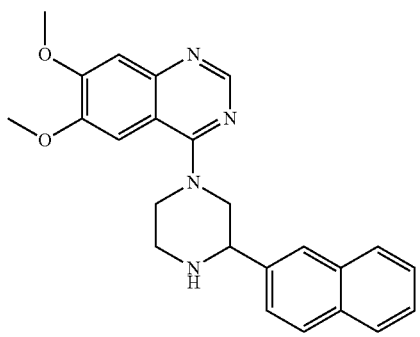 [SMILES: COc1cc2ncnc(N3CCNC(c4ccc5ccccc5c4)C3)c2cc1OC]

The title compound is prepared from 2-naphthalen-2-yl-piperazine and 4-Chloro-6,7-dimethoxy-quinazoline 27. 6,7-Dimethoxy-4-(3-naphthalen-1-yl-piperazin-1-yl)-quinazoline

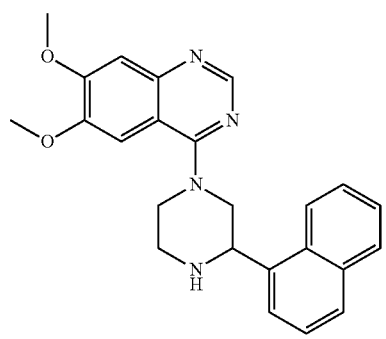 [SMILES: COc1cc2ncnc(N3CCNC(c4cccc5ccccc45)C3)c2cc1OC]

The title compound was prepared from 2-naphthalen-1-yl-piperazine and 4-Chloro-6,7-dimethoxy-quinazoline 28. 4-[3-(3,5-dimethoxyphenyl)-piperazin-1-yl]-6,7-dimethoxy-quinazoline

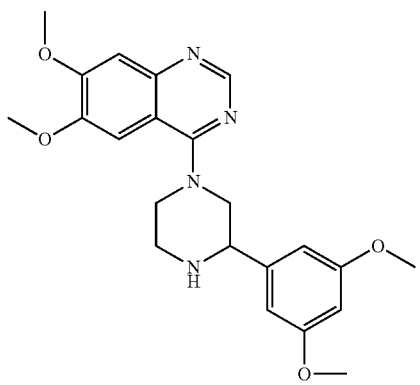

The title compound is prepared from 2-(3,5-dimethoxyphenyl)-piperazine and 4-Chloro-6,7-dimethoxy-quinazoline 29. 4-[3-(2,5-dimethoxyphenyl)-piperazin-1-yl]-6,7-dimethoxy-quinazoline

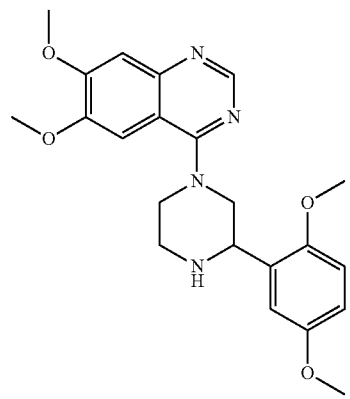

The title compound was prepared from 2-(2,5-dimethoxyphenyl)-piperazine and 4-Chloro-6,7-dimethoxy-quinazoline 30. 4-[3-(4-trifluoromethylphenyl)-piperazin-1-yl]-6,7-dimethoxy-quinazoline

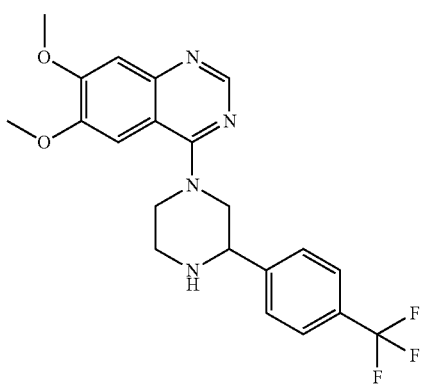 [SMILES: COc1cc2ncnc(N3CCNC(c4ccc(C(F)(F)F)cc4)C3)c2cc1OC]

The title compound is prepared from 2-(4-trifluoromethylphenyl)-piperazine and 4-Chloro-6,7-dimethoxy-quinazoline 31. 4-[3-(2,4-dichlorophenyl)-piperazin-1-yl]-6,7-dimethoxy-quinazoline

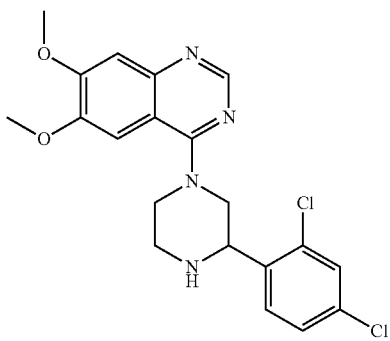 [SMILES: COc1cc2ncnc(N3CCNC(c4ccc(Cl)cc4Cl)C3)c2cc1OC]

The title compound is prepared from 2-(2,4-dichlorophenyl)-piperazine and 4-Chloro-6,7-dimethoxy-quinazoline 32. 4-[3-(3-bromophenyl)-piperazin-1-yl]-6,7-dimethoxy-quinazoline

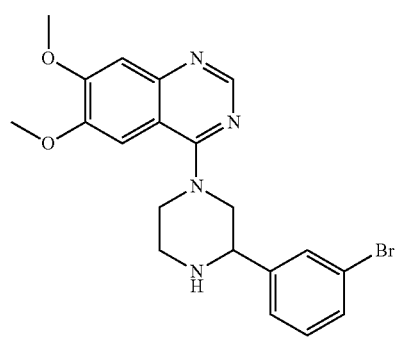 [SMILES: COc1cc2ncnc(N3CCNC(c4cccc(Br)c4)C3)c2cc1OC]

The title compound was prepared from 2-(3-bromophenyl)-piperazine and 4-Chloro-6,7-dimethoxy-quinazoline 34. 4-[3-(4-bromophenyl)-piperazin-1-yl]-6,7-dimethoxy-quinazoline

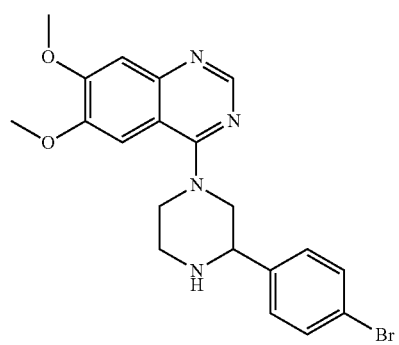 [SMILES: COc1cc2ncnc(N3CCNC(c4ccc(Br)cc4)C3)c2cc1OC]

The title compound was prepared from 2-(4-bromophenyl)-piperazine and 4-Chloro-6,7-dimethoxy-quinazoline 35. 6,7-Dimethoxy-4-(3-(6-methoxy-naphthalen-2-yl)-piperazin-1-yl)-quinazoline

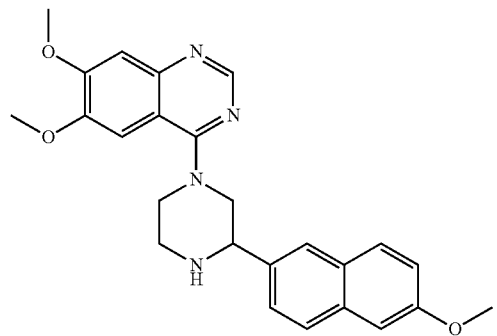

The title compound is prepared from 2-(6-methoxynaph-thalen-2-yl)-piperazine and 4-Chloro-6,7-dimethoxy-quinazoline 36. 6,7-Dimethoxy-4-[3-(4-morpholin-4-yl-phenyl)-piperazin-1-yl]-quinazoline

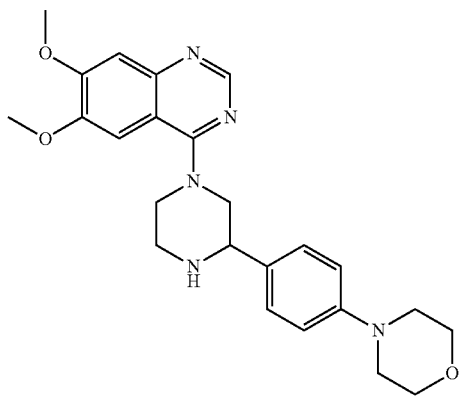 [SMILES: COc1cc2ncnc(N3CCNC(c4ccc(N5CCOCC5)cc4)C3)c2cc1OC]

The title compound is prepared from 4-(4-piperazin-2-yl-phenyl)-morpholine and 4-Chloro-6,7-dimethoxy-quinazoline 37. 4-[3-(2,4-dichloro-5-fluorophenyl)-piperazin-1-yl]-6,7-dimethoxy-quinazoline

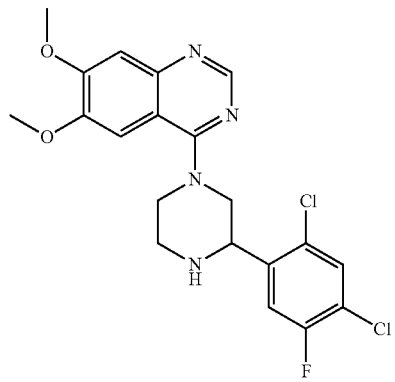 [SMILES: COc1cc2ncnc(N3CCNC(c4cc(F)c(Cl)cc4Cl)C3)c2cc1OC]

The title compound was prepared from 2-(2,4-dichloro-5-fluorophenyl)-piperazine and 4-Chloro-6,7-dimethoxy-quinazoline 38. 6,7-Dimethoxy-4-(2-phenyl-morpholin-4-yl)-quinazoline

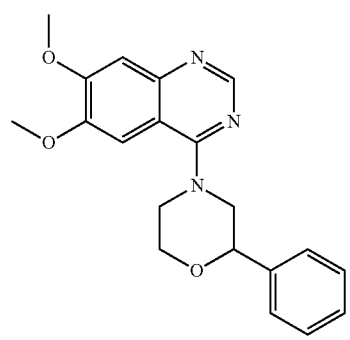

The title compound is prepared from 2-phenyl-morpholine and 4-Chloro-6,7-dimethoxy-quinazoline 39. 6,7-Dimethoxy-4-(2-(2-methoxyphenyl)-morpholin-4-yl)-quinazoline

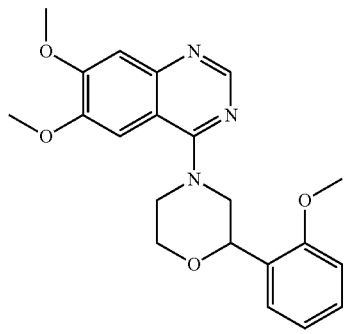

The title compound is prepared from 2-(2-methoxyphenyl)-morpholine and 4-Chloro-6,7-dimethoxy-quinazoline 40. 6,7-Dimethoxy-4-(2-(3,5-dichlorophenyl)-morpholin-4-yl)-quinazoline

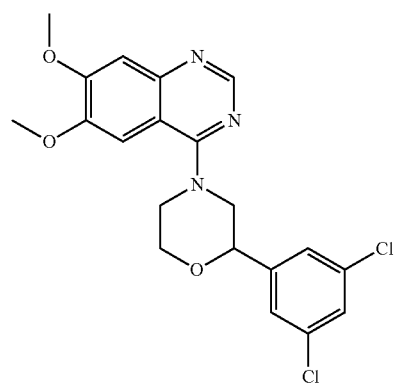 [SMILES: COc1cc2ncnc(N3CCOC(c4cc(Cl)cc(Cl)c4)C3)c2cc1OC]

The title compound is prepared from 2-(3,5-dichlorophenyl)-morpholine and 4-Chloro-6,7-dimethoxy-quinazoline 41. 6,7-Dimethoxy-4-(2-(3,5-dimethoxyphenyl)-morpholin-4-yl)-quinazoline

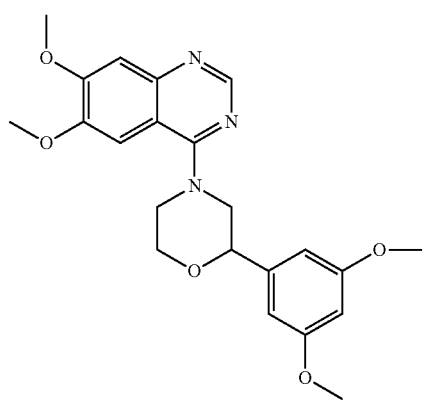

The title compound is prepared from 2-(3,5-dimethoxyphenyl)-morpholine and 4-Chloro-6,7-dimethoxy-quinazoline 42. 6,7-Dimethoxy-4-(2-(4-fluorophenyl)-thiomorpholin-4-yl)-quinazoline

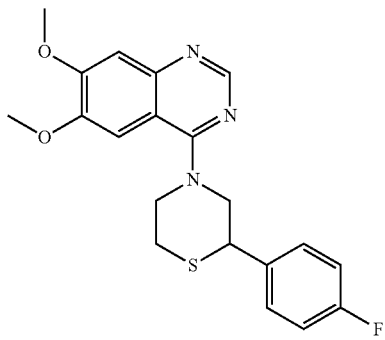

The title compound is prepared from 2-(4-fluorophenyl)-thiomorpholine and 4-Chloro-6,7-dimethoxy-quinazoline 43. 6,7-Dimethoxy-4-(2-(4-chlorophenyl)-thiomorpholin-4-yl)-quinazoline

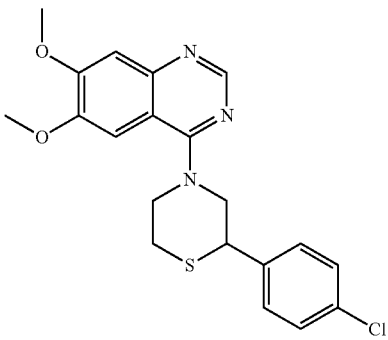 [SMILES: COc1cc2ncnc(N3CCSC(c4ccc(Cl)cc4)C3)c2cc1OC]

The title compound is prepared from 2-(4-chlorophenyl)-thiomorpholine and 4-Chloro-6,7-dimethoxy-quinazoline 44. 6,7-Dimethoxy-4-(2-(2-chlorophenyl)-thiomorpholin-4-yl)-quinazoline

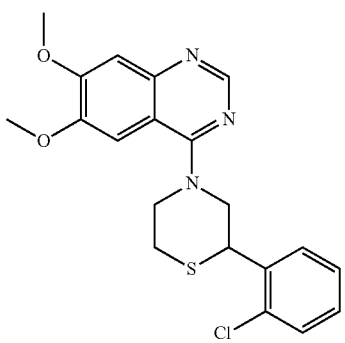 [SMILES: COc1cc2ncnc(N3CCSC(c4ccccc4Cl)C3)c2cc1OC]

The title compound is prepared from 2-(2-chlorophenyl)-thiomorpholine and 4-Chloro-6,7-dimethoxy-quinazoline 45. 6,7-Dimethoxy-4-(2-(4-methoxyphenyl)-thiomorpholin-4-yl)-quinazoline

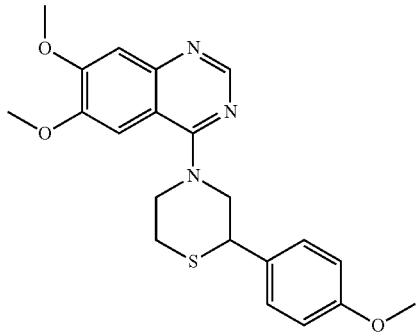

The title compound is prepared from 2-(4-methoxyphenyl)-thiomorpholine and 4-Chloro-6,7-dimethoxy-quinazoline 46. 6,7-Dimethoxy-4-(2-(4-trifluoromethylphenyl)-thiomorpholin-4-yl)-quinazoline

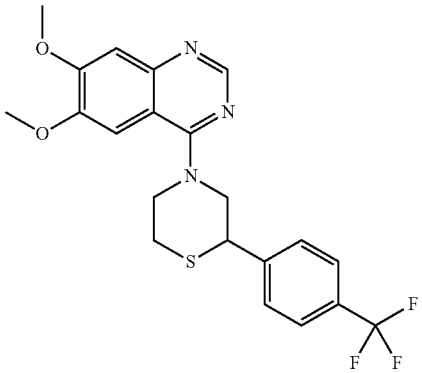 [SMILES: COc1cc2ncnc(N3CCSC(c4ccc(C(F)(F)F)cc4)C3)c2cc1OC]

The title compound is prepared from 2-(4-trifluorophenyl)-thiomorpholine and 4-Chloro-6,7-dimethoxy-quinazoline Pharmacological Testing PDE10A Enzyme Active PDE10A enzyme is prepared in a number of ways for use in PDE assays (Loughney, K. et al. *Gene* 1999, 234, 109-117; Fujishige, K. et al. *Eur J. Biochem.* 1999, 266, 1118-1127 and Soderling, S. et al. *Proc. Natl. Acad. Sci.* 1999, 96, 7071-7076). PDE10A can be expressed as full-length proteins or as truncated proteins, as long as they express the catalytic domain. PDE10A can be prepared in different cell types, for example insect cells or *E. coli*. An example of a method to obtain catalytically active PDE10A is as follows: The catalytic domain of human PDE10A (amino acids 440-779 from the sequence with accession number NP 006652) is amplified from total human brain total RNA by standard RT-PCR and is cloned into the BamH1 and Xho 1 sites of the pET28a vector (Novagen). Expression in coli is performed according to standard protocols. Briefly, the expression plasmids are transformed into the BL21 (DE3) *E. coli* strain, and 50 mL cultures inoculated with the cells allowed to grow to an OD600 of 0.4-0.6 before protein expression is induced with 0.5 mM IPTG. Following induction, the cells are incubated overnight at room temperature, after which the cells are collected by centrifugation. Cells expressing PDE10A are resuspended in 12 mL (50 mM TRIS-HCl-pH8.0, 1 mM MgCl$_2$ and protease inhibitors). The cells are lysed by sonication, and after all cells are lysed, TritonX100 is added according to Novagen protocols. PDE10A is partially purified on Q sepharose and the most active fractions were pooled.

PDE10A Inhibition Assay

PDE10A assays have been described previously (Loughney, K. et al. *Gene* 1999, 234, 109-117; Fujishige, K. et al. *Eur J Biochem.* 1999, 266, 1118-1127 and Soderling, S. et al. *Proc. Natl. Acad. Sci.* 1999, 96, 7071-7076). PDE10A assays could for example can be performed as follows: PDE10A assays are performed in 60 uL samples containing a fixed amount of the relevant PDE enzyme (sufficient to convert 20-25% of the cyclic nucleotide substrate), a buffer (50 mM HEPES7.6; 10 mM MgCl$_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 uL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and IC$_{50}$ values can be calculated using the Xlfit extension to EXCEL.

Results of the experiments showed that the tested compounds of the invention inhibit the PDE10A enzyme with IC$_{50}$ values below 700 nM.

The following table summarizes the analytical data for the exemplified compounds:

What is claimed is:

1. A compound of Formula I

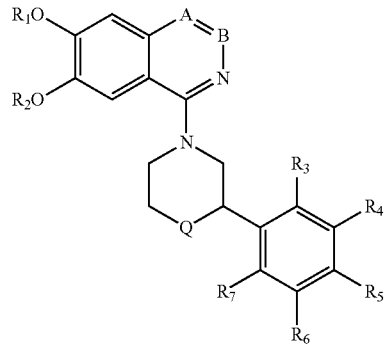

Formula I wherein

Q is NH;

A and B are selected independently from CH and N with the proviso that A and B are not both N at the same time;

$R_1$ and $R_2$ are independently $C_1$-$C_4$ alkyl;

$R_3$, $R_4$, $R_5$, $R_6$ and $R_7$ are independently selected from the group consisting of:

H, ($C_1$-$C_6$) alkyl, ($C_1$-$C_6$) alkoxy, halogen, halo($C_1$-$C_6$) alkyl, ($C_1$-$C_6$)hydroxyalkyl, ($C_1$-$C_6$)alkoxy($C_{1-6}$) alkyl, ($C_1$-$C_6$)hydroxycycloalkyl, ($C_3$-$C_8$)cycloalkoxy, ($C_1$-$C_6$)alkoxy($C_3$-$C_8$)cycloalkyl, heterocycloalkyl, hydroxyheterocycloalkyl, and ($C_1$-$C_6$)alkoxy-heterocycloalkyl, wherein each ($C_3$-$C_8$) cycloalkyl or heterocycloalkyl moiety may be independently substituted with from one to three ($C_1$-$C_6$) alkyl;

| Compound no. | RETENTION TIME | PURITY UV (%) | PURITY ELSD (%) | Measured M + H+ | PDE10 IC50 (nM) |
|---|---|---|---|---|---|
| 1 | 0.92 | 99.891 | 96.901 | 368.2 | 89 |
| 2 | 0.46 | 99.868 | 94.520 | 381.3 | 33 |
| 3 | 0.91 | 100 | 95.039 | 366.2 | 79 |
| 4 | 0.84 | 99.921 | 99.353 | 381.4 | 600 |
| 5 | 0.85 | 98.670 | 99.131 | 381.4 | 14 |
| 6 | 0.79 | 97.883 | 97.348 | 351.3 | 65 |
| 7 | 0.84 | 95.314 | 98.813 | 351.4 | 90 |
| 8 | 0.51 | 96.51 | 100 | 441.4 | 180 |
| 9 | 0.48 | 96.55 | 99.49 | 381.4 | 110 |
| 10 | 0.887 | 97.65 | 100 | 370.2 | 200 |
| 11 | 1.01 | 94.88 | 99.88 | 386.3 | 260 |
| 12 | 1.09 | 95.33 | 100 | 420.3 | 660 |
| 13 | 0.96 | 95.26 | 100 | 386.3 | 190 |
| 14 | 0.75 | 94.326 | 91.560 | 394.3 | 62 |
| 15 | 0.82 | 97.384 | 89.073 | 395 | 35 |
| 16 | 0.9 | 94.918 | 97.613 | 419.4 | 170 |
| 17 | 0.90 | 94.918 | 97.613 | 420.3 | |
| 18 | 0.55 | 91.18 | 100 | 365.4 | |
| 19 | 0.50 | 90.39 | 100 | 369.4 | |
| 20 | 0.64 | 91.56 | 99.45 | 379.5 | |
| 21 | 0.50 | 88.97 | 99.64 | 381.4 | |
| 22 | 0.58 | 89.1 | 98.58 | 385.9 | |
| 24 | 0.50 | 90.5 | 99.01 | 396.4 | |
| 27 | 0.63 | 98.65 | 100 | 401.5 | |
| 29 | 0.52 | 99.140 | 98.461 | 411.5 | |
| 32 | 0.76 | 98.99 | 100 | 427.5 | |
| 34 | 0.61 | 99.48 | 100 | 430.3 | |
| 37 | 0.69 | 82.31 | 97.09 | 438.3 | | a —NR$_8$R$_9$ group, wherein R$_8$ and R$_9$ are independently selected from the group consisting of hydrogen, C$_1$-C$_6$ alkyl, halo(C$_1$-C$_6$)alkyl, (C$_3$-C$_8$)cycloalkyl, and heterocycloalkyl; and a 6-7-membered aliphatic heterocycle:

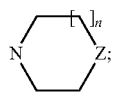

wherein n is 1 or 2 and Z is oxygen or NR$_{10}$, wherein R$_{10}$ is selected from the group consisting of hydrogen, (C$_1$-C$_6$) alkyl,

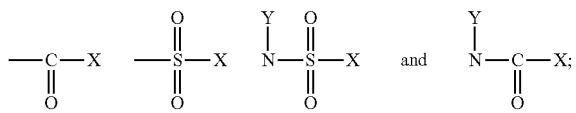

wherein Y is hydrogen or (C$_1$-C$_6$) alkyl and X is selected from the group consisting of:
a (C$_1$-C$_6$) alkyl group unsubstituted or substituted with one or more halogens,
—O—(C$_1$-C$_6$) alkyl unsubstituted or substituted with one or more halogens,
a —NR$_{11}$R$_{12}$ group, where R$_{11}$ and R$_{12}$ are independently selected from hydrogen, C$_1$-C$_6$ alkyl, halo(C$_1$-C$_6$)alkyl, (C$_3$-C$_8$)cycloalkyl, heterocycloalkyl, and
a 6-7-membered aliphatic heterocycle:

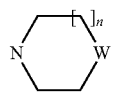

wherein n is 1 or 2; and W is oxygen or NR$_{13}$, wherein R$_{13}$ is hydrogen or (C$_1$-C$_6$) alkyl, or
two adjacent substituents selected from R$_3$, R$_4$, R$_5$, R$_6$ and R$_7$ may together with the aromatic ring they are attached to form a 5-7 membered, saturated or unsaturated ring containing carbon and one or two heteroatoms selected from N, O or S, and optionally substituted with an (C$_1$-C$_6$) alkoxy group where the remaining three substituents selected from R$_3$, R$_4$, R$_5$, R$_6$ and R$_7$, which do not take part of the ring, are independently selected as stated above;
or a pharmaceutically acceptable salt thereof.

2. The compound of claim 1 in which A is N and B is CH.
3. The compound of claim 1 in which A is CH and B is CH.
4. The compound of claim 1 in which A is CH and B is N.
5. The compound of claim 1 wherein R$_1$ and R$_2$ are independently C$_1$-C$_2$ alkyl.
6. The compound of claim 1 wherein R$_3$ is selected from the group consisting of H, (C$_1$-C$_6$) alkoxy and halogen.
7. The compound of claim 1 wherein R$_4$ is selected from the group consisting of H, (C$_1$-C$_6$) alkoxy, halogen and nitro.
8. The compound of claim 1 wherein R$_5$ is selected from the group consisting of
hydrogen, (C$_1$-C$_6$) alkyl, (C$_1$-C$_6$) alkoxy, halogen, halo(C$_1$-C$_6$)alkyl, nitro, or a —NR$_8$R$_9$ group, where R$_8$ and R$_9$ are independently selected from hydrogen, C$_1$-C$_6$ alkyl, halo(C$_1$-C$_6$)alkyl, (C$_3$-C$_8$)cycloalkyl, heterocycloalkyl, and
a 6-7-membered aliphatic heterocycle:

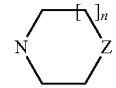

wherein n is 1 or 2 and Z is oxygen or NR$_{10}$, wherein R$_{10}$ is hydrogen or (C$_1$-C$_6$) alkyl.

9. The compound of claim 1 wherein R$_6$ is selected from the group consisting of H, (C$_1$-C$_6$) alkoxy, halogen and nitro.
10. The compound of claim 1 wherein R$_7$ is selected from the group consisting of H, (C$_1$-C$_6$) alkoxy and halogen.
11. The compound of claim 1 wherein two adjacent substituents selected from R$_3$, R$_4$, R$_5$, R$_6$ and R$_7$, together with the aromatic ring they are attached to, form a 5-7 membered, saturated or unsaturated ring, optionally containing one or two heteroatoms selected from N, O or S.
12. The compound of claim 1, wherein the compound is selected from the group consisting of 6,7-Dimethoxy-4-(3-(3-methoxyphenyl)-piperazin-1-yl)-quinazoline; 6,7-Dimethoxy-4-((R)-3-(3-methoxyphenyl)-piperazin-1-yl)-quinazoline; 6,7-Dimethoxy-4-((S)-3-(3-methoxyphenyl)-piperazin-1-yl)-quinazoline; 6,7-Dimethoxy-4-((R)-3-phenyl-piperazin-1-yl)-quinazoline; 6,7-Dimethoxy-4-((S)-3-phenyl-piperazin-1-yl)-quinazoline; 4-[3-(3,4,5-trimethoxyphenyl)-piperazin-1-yl]-6,7-dimethoxy-quinazoline; 4-[3-(2-methoxyphenyl)-piperazin-1-yl]-6,7-dimethoxy-quinazoline; 4-[3-(4-dimethylaminophenyl)-piperazin-1-yl]-6,7-dimethoxy-quinazoline; 4-[3-(3,4-methylendioxyphenyl)-piperazin-1-yl]-6,7-dimethoxy-quinazoline; 4-[3-(4-methylphenyl)-piperazin-1-yl]-6,7-dimethoxy-quinazoline; 4-[3-(4-fluorophenyl)-piperazin-1-yl]-6,7-dimethoxy-quinazoline; 4-[3-(4-ethylphenyl)-piperazin-1-yl]-6,7-dimethoxy-quinazoline; 4-[3-(4-methoxyphenyl)-piperazin-1-yl]-6,7-dimethoxy-quinazoline; 4-[3-(4-chlorophenyl)-piperazin-1-yl]-6,7-dimethoxy-quinazoline; 4-[3-(3-chlorophenyl)-piperazin-1-yl]-6,7-dimethoxy-quinazoline; 4-[3-(3-nitrophenyl)-piperazin-1-yl]-6,7-dimethoxy-quinazoline; 4-[3-(4-nitrophenyl)-piperazin-1-yl]-6,7-dimethoxy-quinazoline; 6,7-Dimethoxy-4-(3-naphthalen-2-yl-piperazin-1-yl)-quinazoline; 6,7-Dimethoxy-4-(3-naphthalen-1-yl-piperazin-1-yl)-quinazoline; 4-[3-(3,5-dimethoxyphenyl)-piperazin-1-yl]-6,7-dimethoxy-quinazoline; 4-[3-(2,5-dimethoxyphenyl)-piperazin-1-yl]-6,7-dimethoxy-quinazoline; 4-[3-(4-trifluoromethylphenyl)-piperazin-1-yl]-6,7-dimethoxy-quinazoline; 4-[3-(2,4-dichlorophenyl)-piperazin-1-yl]-6,7-dimethoxy-quinazoline; 4-[3-(3-bromophenyl)-piperazin-1-yl]-6,7-dimethoxy-quinazoline; 4-[3-(4-bromophenyl)-piperazin-1-yl]-6,7-dimethoxy-quinazoline; 6,7-Dimethoxy-4-(3-(6-methoxy-naphthalen-2-yl)-piperazin-1-yl)-quinazoline; 4-[3-(2,4-dichloro-5-fluorophenyl)-piperazin-1-yl]-6,7-dimethoxy-quinazoline; or a pharmaceutically acceptable salt thereof.

13. A pharmaceutical composition comprising a therapeutically effective amount of a compound of claim 1 and a pharmaceutically acceptable carrier or diluent.
14. A compound, wherein the compound is 4-[3-(2,5-dichlorophenyl)-piperazin-1-yl]-6,7-dimethoxy-quinazoline.

* * * * *